(12) United States Patent
Nitzan et al.

(10) Patent No.: US 7,643,874 B2
(45) Date of Patent: Jan. 5, 2010

(54) DERMAL PATCH (75) Inventors: Zvi Nitzan, Zofit (IL); Yossi Gross, Moshav Mazor (IL); Daniela Mavor, Tel Aviv (IL); Dov Tamarkin, Maccabim (IL)

(73) Assignee: Power Paper Ltd., Petah Tikva (IL)

( * ) Notice: Subject to any disclaimer, the term of this patent is extended or adjusted under 35 U.S.C. 154(b) by 1041 days.

(21) Appl. No.: 10/757,414

(22) Filed: Jan. 15, 2004

(65) Prior Publication Data

US 2004/0167461 A1  Aug. 26, 2004

Related U.S. Application Data (63) Continuation-in-part of application No. PCT/IL02/00848, filed on Oct. 23, 2002.

(60) Provisional application No. 60/330,526, filed on Oct. 24, 2001.

(51) Int. Cl.
 *A61M 1/30* (2006.01)
(52) U.S. Cl. .................................................. 604/20
(58) Field of Classification Search ............ 604/19–20, 604/501, 500, 890.1–892.1
See application file for complete search history.

(56) References Cited

U.S. PATENT DOCUMENTS

| 4,927,408 A | * | 5/1990 | Haak et al. ............... 604/20 |
| 5,601,618 A | | 2/1997 | James |
| 5,652,043 A | | 7/1997 | Nitzan ................... 428/209 |
| 5,800,685 A | | 9/1998 | Perrault ................. 204/291 |
| 5,897,522 A | | 4/1999 | Nitzan ..................... 604/20 |
| 6,238,381 B1 | | 5/2001 | Tapper .................. 604/501 |

FOREIGN PATENT DOCUMENTS

| RU | 2156142 C1 | 9/2000 |
| SU | 1780513 A3 | 7/1992 |
| WO | WO 93/00959 A | 1/1993 |
| WO | WO 98/56458 | 12/1998 |
| WO | WO 9856458 A1 | 12/1998 |
| WO | WO 00/54834 A | 9/2000 |
| WO | WO 03/035166 A | 5/2003 |
| WO | WO 03/035167 A | 5/2003 |

* cited by examiner

*Primary Examiner*—Manuel A Mendez
(74) *Attorney, Agent, or Firm*—Kenyon & Kenyon LLP (57) ABSTRACT

The invention is generally directed to a kit and patch for transdermal or intradermal delivery of at least one substance into the skin. The kit includes a dermal patch having an electrochemical cell with two electrodes and a retainer for retaining a conductive fluid which further includes an active substance. The conductive fluid can be deposited on at least one of the two electrodes. Alternatively, the conductive fluid can be applied topically to the skin.

34 Claims, 5 Drawing Sheets

DERMAL PATCH

CROSS REFERENCE TO RELATED APPLICATIONS

This application is a continuation-in-part of PCT/IL02/00848 filed Oct. 23, 2002, which claims priority to U.S. Provisional Application No. 60/330,526 filed Oct. 24, 2001, the entire contents of which are incorporated herein.

FIELD AND BACKGROUND OF THE INVENTION

The present invention relates to transdermal and/or intradermal drug delivery devices, kits and methods and, more particularly, to a dermal patch which is capable of delivering an electric current for electrically including transdermal and intradermal delivery of a wide variety of substances or for enhancement of wound healing, scar prevention, scar reduction, tissue repair and/or tissue regeneration via electrical stimulation.

Much recent attention has been paid in the technical and patent literature to the delivery of substances, both pharmaceuticals and cosmetics, such as drugs and other beneficial agents, into or through intact skin surfaces by passive processes such as diffusion and osmosis and by active processes such as electrically induced iontophoresis, electrophoresis, electroosmosis and/or electroporation. The ubiquitous nicotine patch designed to assist in quitting smoking has caused such forms of transdermal delivery of medication to be widely known. (Hereunder, the term "iontophoresis" will collectively represent any of the terms iontophoresis, electrophoresis, electroosmosis and/or electroporation, and the term "iontophoretic" will encompass the respective adjectives.)

Indeed, there is now an extremely long list of pharmaceutical substances that are routinely administered transdermally and/or intradermally and a similarly long list of devices and methods known in the art for administering same. A short but varied sampling includes the following: U.S. Pat. No. 6,294,582 which discloses a device for treating asthma transdermally; U.S. Pat. No. 5,899,856 which discloses a dermal patch for detecting alcohol consumption; U.S. Pat. No. 6,291,677 which teaches the transdermal administration of antiviral protease inhibitors; U.S. Pat. No. 6,266,560 which discloses the transdermal treatment of erectile dysfunction; U.S. Pat. No. 6,238,381 which discloses the transdermal delivery of antiviral, antibacterial and antiaging substances; and U.S. Pat. No. 6,288,104 which discloses the transdermal administration of substances for treating congestive heart failure.

Although many substances are administered passively via a dermal patch, there are also many that are electrically delivered intradermally or transdermally.

The use of electrical stimulus to body parts is well known and has an equally long and colorful history. Around the turn of the 20th century there was available a plethora of "electrodes" for applying "electric treatments" to the human body. The electrodes were placed upon the body in relation to the organ to be treated. Such early "electric treatments" included popular galvanic stimulation which caused ionized molecules to be driven into the body, usually superficially. This early form of iontophoresis, or ion transfer, was employed for the supposed beneficial effects of localized stimulation and the introduction of medicaments, often simply moisture, into the skin of a patient.

The technique of iontophoresis is in wide use today in the administration of drugs as it effectively delivers electrically charged medicaments through the skin, and into the capillary structure and lymphatic system. This technique avoids the gastrointestinal side effects sometimes associated with orally ingested drugs and is preferable to subcutaneous injection because of its relatively benign and painless nature.

Another technique, known as electroporation, facilitates the transdermal or intradermal delivery of uncharged substances by electrically inducing the formation of transient dermal micropores that allow mobilization of the uncharged substances by diffusion.

Accordingly, iontophoresis, as well as other electrically induced techniques, such as electroporation, has been incorporated into many transdermal delivery devices, including the popular dermal patch. Therefore, there are many dermal patches known in the art today which incorporate a power source and electrical circuitry for aiding transdermal delivery.

Most present dermal patches, including those that function passively and those that function electrically, incorporate a substance for transdermal delivery. Such patches are specifically designed and/or configured to deliver a predetermined dosage of a specific substance, and that substance forms an integral part of the patch in question, i.e., the "nicotine patch". One drawback of such dermal patches, which are manufactured with a predetermined type and amount of substance therein is that once the substance is depleted, the entire device is useless and must be discarded. This is a disadvantage because patches which employ electrically induced delivery techniques necessarily have components, e.g., batteries, electrodes, circuitry and other assemblies, which may be expensive and/or environmentally hazardous when discarded in large quantities. Also, in order to change dosage, patches of different dosages must be provided.

There is also known in the art today a range of reusable dermal patches that incorporate a reservoir for holding a medicinal substance prior to administration. Those dermal patches typically incorporate the reservoir as part of one or both of the electrodes which deliver the current to the skin of the subject. Such electrodes are often referred to as bioelectrodes.

Bioelectrodes come in many sizes, shapes and configurations such as the following assigned to Ioimed, Inc., which produces iontophoretic delivery devices. Examples of such bioelectrodes include those disclosed in U.S. Pat. Nos. 5,037,380 and 5,248,295 which teach a patch having a refillable receptacle; U.S. Pat. No. 5,846,217 which teaches a patch having a small access window for refilling; and U.S. Pat. Nos. 5,374,245, 5,730,716 and 6,223,075 which teach a patch that holds a dry medicament and must be hydrated. All such bioelectrodes are complex and consist of many parts and are therefore relatively bulky. Accordingly, those that are incorporated into dermal patches cause the patches to be large and relatively expensive. Moreover, such dermal patches must be charged, or loaded, by a clinician and not by the subject.

There is thus a widely recognized need for, and it would be highly advantageous to have, a thin, flexible and simple electrically active dermal patch that is simple to administer by the subject, versatile and capable of application with a range of substances and/or dosages and for a variety of purposes and that is simple in design and inexpensive to manufacture.

SUMMARY OF THE INVENTION

Accordingly, it is an object of the present invention to provide a versatile dermal patch that incorporates a power source that may be used to transdermally or intradermally deliver a range of different substances.

It is a further object of the present invention to provide a versatile dermal patch that incorporates a power source that may be used to introduce an electric current to a skin portion for a variety of purposes.

It is a further object of the present invention to provide a versatile dermal patch that incorporates a thin and flexible power source that may be used to introduce an electric current to a skin portion for a variety of purposes and/or that may be used to transdermally or intradermally deliver a range of different substances.

According to one aspect of the present invention there is provided a kit for transdermal or intradermal delivery of at least one substance, the kit comprising (a) a dermal patch which comprises an electrochemical cell having at least two electrodes positioned on one side of the dermal patch for forming electrical contact with a skin portion of a subject; and (b) at least one retainer for retaining a conductive fluid containing the substance, the conductive fluid being for deposition on at least one of the electrodes and/or topical application onto the skin portion of the subject; the patch being designed and configured for delivering an electric current for transdermal or intradermal delivery of the substance through the conductive fluid and the skin of the subject.

According to another aspect of the present invention there its provided a kit for introduction of current and/or voltage to a skin portion of a subject, the kit comprising (a) a dermal patch which comprises an electrochemical cell having at least two electrodes positioned on one side of the dermal patch for forming electrical contact with the skin portion of the subject; and (b) at least one retainer for retaining a conductive fluid for deposition on at least one of the electrodes and/or topical application onto the skin portion of the subject; the patch being designed and configured for delivering an electric current for introduction of current and/or voltage to the skin portion of the subject through the conductive fluid.

According to yet another aspect of the present invention there is provided a dermal patch consisting essentially of an electrochemical cell having at least two electrodes positioned on one side of the dermal patch for forming electrical contact with a skin portion of a subject, the dermal patch being designed and configured for delivering an electric current through a conductive fluid being deposited on at least one of the electrodes and/or being topically applied onto the skin portion of the subject.

According to a further aspect of the present invention there is provided a method of transdermal or intradermal delivery of a substance comprising (a) topically applying a conductive fluid containing the substance into a skin portion of the subject and/or depositing the conductive fluid containing the substance on at least one electrode of a dermal patch which comprises an electrochemical cell having at least two electrodes positioned on one side of the dermal patch; (b) positioning the dermal patch such that the electrodes are in electrical contact with the skin portion of the subject; and (c) delivering an electric current through the conductive fluid and the skin portion so as to transdermally or intradermally deliver the substance.

According to a yet further aspect of the present invention there is provided a method of introducing current and/or voltage to a skin portion of a subject comprising (a) topically applying a conductive fluid onto a skin portion of the subject and/or depositing the conductive fluid on at least one electrode of a dermal patch which comprises an electrochemical cell having at least two electrodes positioned on one side of the dermal patch; (b) positioning the dermal patch such that the electrodes are in electrical contact with the skin portion of a subject; and (c) delivering an electric current through the conductive fluid so as to introduce current and/or voltage to the skin portion of the subject.

According to features in the described preferred embodiments the conductive fluid is an aqueous based fluid.

According to features in the described preferred embodiments the conductive fluid is a hydrogel.

According to features in the described preferred embodiments the conductive fluid is selected from the group consisting of a gel, a cream, a paste, a lotion, a suspension, an emulsion and a solution.

According to features in the described preferred embodiments the conductive fluid is for deposition on at least one of the two electrodes.

According to features in the described preferred embodiments the conductive fluid is for topical application to the skin portion of a subject.

According to features in the described preferred embodiments the substance is a charged substance.

According to features in the described preferred embodiments the substance is an uncharged substance.

According to features in the described preferred embodiments the substance is selected from the group consisting of a pharmaceutical, a cosmetic and a cosmeceutical.

According to features in the described preferred embodiments the pharmaceutical is selected from the group consisting of a therapeutic and an anesthetic.

According to features in the described preferred embodiments the electric current serves for causing iontophoresis, electrophoresis, electroporation or any combination thereof.

According to features in the described preferred embodiments the electric current is for causing wound healing, scar prevention, scar reduction, body tissue repair and/or tissue regeneration.

According to features in the described preferred embodiments the retainer is selected from the group consisting of a vessel, a tube, a jar, a container, a dispenser and an ampoule.

According to features in the described preferred embodiments the retainer is a separator for deposition upon at least one of the two electrodes.

According to features in the described preferred embodiments the electric current delivers the substance from the separator. Such separator is intended to prevent contact between the electrode and the skin and to provide an even distribution of the electric current over the entire surface of the patch. Such separator being either an integral part of the electrode or attached thereto.

According to features in the described preferred embodiment the separator is contained in a removable cover.

According to features in the described preferred embodiments the electrochemical cell is a flexible thin layer electrochemical cell.

According to features in the described preferred embodiments the electrochemical cell is a flexible thin layer open liquid state electrochemical cell which includes a first layer of insoluble negative pole, a second layer of insoluble positive pole and a third layer of aqueous electrolyte, the third layer being disposed between the first and second layers and including (a) a deliquescent material for keeping the open cell wet at all times; (b) an electroactive soluble material for obtaining required ionic conductivity; and (c) a water-soluble polymer for obtaining a required viscosity for adhering the first and second layers to the third layer.

According to features in the described preferred embodiments at least one of the two electrodes is for mobilizing the at least one substance.

According to features in the described preferred embodiments the at least two electrodes are integrally formed with the electrochemical cell.

According to features in the described preferred embodiments the electrochemical cell and the at least two electrodes are the sole constituents of the patch.

According to features in the described preferred embodiments the dermal patch further includes an attachment mechanism for attaching to the skin portion of the subject.

According to features in the described preferred embodiments the dermal patch is for use in the treatment of hyperhidrosis.

According to features in the described preferred embodiments the dermal patch further includes a circuitry for controlling the electric current.

According to features in the described preferred embodiments the kit is packaged and identified for a wound healing application, a scar prevention application, a scar reduction application, a tissue repair application, a tissue regeneration application, a transdermal delivery application and an intradermal delivery application.

The present invention successfully addresses the shortcomings of the presently known configurations by providing a versatile dermal patch, operable in transdermal and/or intradermal delivery with any number of substances and dosages.

According to a still further aspect of the present invention there is provided a kit for treatment of hyperhidrosis, the kit including: (a) a dermal patch which includes an electrochemical cell having at least two electrodes positioned on one side of the dermal patch, the electrodes being for forming electrical contact with a skin portion of a subject; and (b) at least one retainer for retaining a conductive fluid containing at least one substance, the conductive fluid being for deposition on at least one of the at least two electrodes and/or topical application onto the skin portion of the subject; the patch being designed and configured for delivering an electric current through the skin and the conductive fluid, the electric current being for treatment of hyperhidrosis.

According to features of the kit for the treatment of hyperhidrosis in the described preferred embodiments, the conductive fluid contains water.

According to features of the kit for the treatment of hyperhidrosis in the described preferred embodiments, the conductive fluid comprises an antihyperhidrosis active substance.

According to a yet further aspect of the present invention there is provided a device for introduction of water to a skin portion of a subject, the device including: a dermal patch including an electrochemical cell wherein the electrochemical cell is a flexible thin layer open liquid state electrochemical cell which includes a first layer of insoluble negative pole, a second layer of insoluble positive pole and a third layer of aqueous electrolyte, the third layer being disposed between the first and second layers and including: (a) a deliquescent material for keeping the open cell wet at all times; (b) an electroactive soluble material for obtaining required ionic conductivity; and (c) water-soluble polymer for obtaining a required viscosity for adhering the first and the second layers to the third layer, having at least two electrodes positioned on one side of the dermal patch, the electrodes being for forming electrical contact with the skin portion of the subject; and the patch being designed and configured for delivering an electric current through the skin, the electric current being for introduction of water to the skin portion of the subject.

According to another aspect of the present invention there is provided a device for treatment of hyperhidrosis, the device comprising: a dermal patch comprising an electrochemical cell having at least two electrodes positioned on one side of the dermal patch, the electrodes being for forming electrical contact with the skin portion of the subject; and the patch being designed and configured for delivering an electric current through the skin, the electric current being for delivery of ions into the skin portion of the subject and for treatment of hyperhidrosis.

According to a still further aspect of the present invention there is provided a device for treatment of hyperhidrosis, the device comprising: a dermal patch comprising an electrochemical cell wherein the electrochemical cell is a small and thin electrochemical cell having at least two electrodes positioned on one side of the dermal patch, the electrodes being for forming electrical contact with the skin portion of the subject; and the patch being designed and configured for delivering an electric current through the skin, the electric current being for delivery of ions into the skin portion of the subject and for treatment of hyperhidrosis.

According to a yet further aspect of the present invention there is provided a device for treatment of hyperhidrosis, the device including: a dermal patch including an electrochemical cell wherein the electrochemical cell is a flexible thin layer open liquid state electrochemical cell which includes a first layer of insoluble negative pole, a second layer of insoluble positive pole and a third layer of aqueous electrolyte, the third layer being disposed between the first and second layers and including: (a) a deliquescent material for keeping the open cell wet at all times; (b) an electroactive soluble material for obtaining required ionic conductivity; and (c) a water-soluble polymer for obtaining a required viscosity for adhering the first and the second layers to the third layer, having at least two electrodes positioned on one side of the dermal patch, the electrodes being for forming electrical contact with the skin portion of the subject; and the patch being designed and configured for delivering an electric current through the skin, the electric current being for delivery of ions into the skin portion of the subject and for treatment of hyperhidrosis.

According to a yet further aspect of the present invention there is provided an iontophoretic patch for transdermal or intradermal delivery of at least one substance, the patch including: an electrochemical cell for powering the patch; at least two electrodes in electrical contact with the electrochemical cell; and a conductive fluid, wherein the conductive fluid is preapplied to the at least two electrodes; and wherein on contacting the patch with skin an electric current is delivered through the conductive fluid and skin of a subject so as to transdermally or intradermally deliver the at least one substance.

According to features of the iontophoretic patch in the described preferred embodiments the conductive fluid is aqueous hydrogel.

According to features of the iontophoretic patch in the described preferred embodiments, the one substance is water.

According to features of the iontophoretic patch in the described preferred embodiments, the one substance is an antihyperhidrosis active substance.

According to a yet further aspect of the present invention there is provided an iontophoretic patch for transdermal or intradermal delivery of water, the patch including: an electrochemical cell for powering the patch; at least two electrodes in electrical contact with the electrochemical cell; and an aqueous conductive fluid, wherein the aqueous conductive fluid is preapplied to the at least two electrodes; and wherein on contacting the patch with skin an electric current is delivered through the aqueous conductive fluid and skin of a subject so as to transdermally or intradermally deliver water from the aqueous conductive fluid.

BRIEF DESCRIPTION OF THE DRAWINGS

With specific reference now to the drawings in detail, it is stressed that the particulars shown are by way of example and for the purposes of illustrative discussion of the preferred embodiment of the present invention only, and are presented in the cause of providing what is believed to be the most useful and readily understood description of the principles and conceptual aspects of the invention. In this regard, no attempt is made to show structural details of the invention in more detail that is necessary for a fundamental understanding of the invention, the description taken with the drawings making apparent to those skilled in the art how the several forms of the invention may be embodied in practice.

In the drawings:

FIGS. 3a-d illustrate a first foolproof embodiment according to the present invention;

FIGS. 5a-c illustrate a third foolproof embodiment according to the present invention.

DESCRIPTION OF THE PREFERRED EMBODIMENTS

The present invention is of kits, dermal patches and methods which can be used for transdermal and/or intradermal delivery of a variety of substances, such as pharmaceuticals, cosmetics and cosmeceuticals, by means of iontophoresis, electrophoresis and/or electroporation. A dermal patch of the present invention is advantageously versatile in the sense that single patch is operative for transdermal and/or intradermal delivery of a versatile range of substances and/or dosages and that the patch may be simply charged and administered by the subject.

Before explaining at least one embodiment of the invention in detail, it is to be understood that the invention is not limited in this application to the details of construction and the arrangement of the components set forth in the following description or illustrated in the drawings. The inventions is applicable to other, embodiments or of being practiced or carried out in various ways. Also, it is to be understood that the phraseology and terminology employed herein is for the purpose of description and should not be regarded as limiting.

The principles and operation of a kit for transdermal and intradermal delivery of a substance and a kit for the introduction of current and/or voltage to a skin portion of a subject according to the present invention many be better understood with reference to the drawings and accompanying descriptions.

Figure 1:
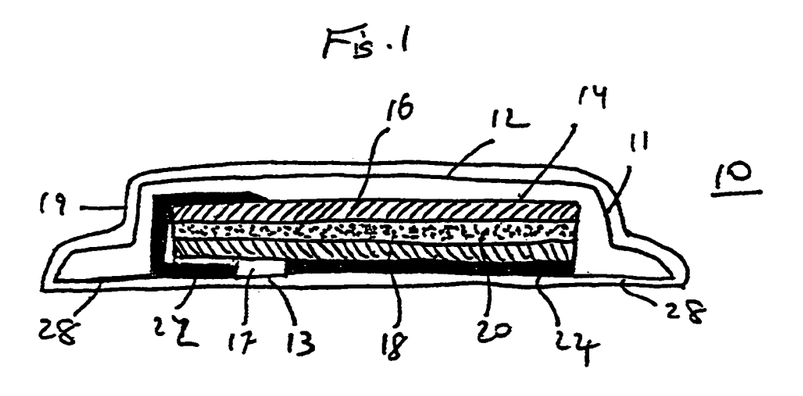
FIG. 1 is a sectional view of a dermal patch constructed in accordance with a preferred embodiment of the present invention.

Reference is now made to FIG. 1, which shows a dermal patch in accordance with the teachings of the present invention, which is referred to herein below as patch 10. Patch 10 includes a top surface 12 and a skin contacting bottom surface 13, which together form patch body 11. Patch 10 is preferably fabricated from flexible materials, which enable surface 12 and/or 13 to conform to the contours of a subject's skin portion when patch 10 is applied thereon. It is understood that patch body 11 may be of any size and shape necessary according to the relevant application.

Patch 10 preferably further includes a skin attachment mechanism, which is preferably an adhesive layer 28 which serves for attaching patch 10 to a skin portion of the subject. Adhesive layer 28 covers at least a portion of bottom surface 13 of patch 10. Adhesive layer 28 preferably includes a biocompatible permeable pressure sensitive adhesive such as Bio-PSA from Dow Corning. Other examples of biocompatible adhesives will be readily apparent to those of ordinary skill in the art. Adhesive layer 28 may be useful for either a single attachment or repeated attachments.

Patch 10 includes therein an electrochemical cell 14, which is preferably a flexible thin electrochemical cell, most preferably an open, liquid state electrochemical cell. It is appreciated that patch 10 may employ any other electrochemical cell or power generating device that serves to provide the needed electric current for the relevant application. Numerous types of miniature power sources, both disposable and rechargeable, which can be incorporated into patch body 11 are known in the art.

According to a preferred embodiment of the present invention electrochemical cell 14 is a thin flexible electrochemical cell, which engages most of the entire volume of patch body 11. In the presently preferred embodiment, electrochemical cell 14 includes a positive pole layer 16, a negative pole layer 18 and an electrolyte layer 20 interposed therebetween. An example of a suitable thin and flexible electrochemical cell is described, for example, in U.S. Pat. Nos. 5,652,043, 5,897, 522 and 5,811,204, which are incorporated herein by reference. Briefly, the electrochemical cell described in the above identified U.S. Patents is an open liquid state, electrochemical cell which can be used as a primary or rechargeable power source for various miniaturized and portable electrically powered devices of compact design. The cell includes a first layer of insoluble negative pole, a second layer of insoluble positive pole and a third layer of aqueous electrolyte being disposed between the first and second layers and including (a) a deliquescent material for keeping the open cell wet at all times; (b) an electroactive soluble material for obtaining required ionic conductivity; and, (c) a water-soluble polymer for obtaining a required viscosity for adhering the first and second layers to the third layer.

Several preferred embodiments of the disclosed electrochemical cell include (i) engaging the electrolyte layer in a porous substance, such as, but not limited to, a filter paper, a plastic membrane, a cellulose membrane and a cloth; (ii) having the first layer of insoluble positive pole include manganese-dioxide powder and the second layer of insoluble negative pole include zinc powder; (iii) having the first layer of insoluble negative pole and/or the second layer of insoluble positive pole further include carbon powder; (iv) selecting the electroactive soluble from zinc-chloride, zinc-bromide, zinc-fluoride and potassium-hydroxide; (v) having the first layer of insoluble negative pole include silver-oxide powder and the second layer of insoluble positive pole include zinc powder and the electroactive soluble material is potassium-hydroxide; (vi) having the first layer of insoluble negative pole include cadmium powder and the second layer of insoluble positive pole include nickel-oxide powder and selecting the electroactive soluble material to be potassium-hydroxide; (vii) having the first layer of insoluble negative pole include iron powder and the second layer of insoluble positive pole include nickel-oxide powder and selecting the electroactive soluble material to be potassium-hydroxide; (viii) having the first layer of insoluble negative pole and the second layer, of insoluble positive pole include lead-oxide powder, then cell is charged by voltage applied to the poles and the electroactive soluble material is selected in this case to be sulfuric-acid; (ix)

the deliquescent material and the electroactive soluble material can, be the same material such as zinc-chloride, zinc-bromide, zinc-fluoride and potassium-hydroxide; (x) the deliquescent material is selected from the group consisting of calcium-chloride, calcium-bromide, potassium-biphosphate and potassium-acetate; (xi) the water-soluble polymer can be polyvinyl alcohol, polyacrylamide, polyacrylic acid, polyvinylpyrrolidone, polyethylenoxide, agar, agarose, starch, hydroxyethylcellulose and combinations and copolymers thereof; (xii) the water-soluble polymer and the deliquescent material can be the same material such as dextrane, dextranesulfate and combinations and copolymer thereof. Electrochemical cell 14 preferably incorporates any one or more of the embodiments described above. Preferred configurations for electrochemical cell 14 according to the present invention involve those combinations which are devoid of poisonous compounds.

Electrochemical cell 14 includes terminals serving as electrodes referred to hereinafter as positive electrode 22 and negative electrode 24 each of which being in electrical contact with positive pole layer 16 and negative pole layer 18, respectively. Electrodes 22 and 24 are electrically connected to electrochemical cell 14 using well known means, e.g., printed flexible circuits, metal foils, wires, electrically conductive adhesives or by direct contact. It is understood that measures are taken to avoid contact between the electrodes and between each of the electrodes and the opposite pole layer. In FIG. 1, the measure taken is the interposition of insulating element 17 formed of a dielectric material.

Electrodes 22 and 24 are electrically conductive and may be formed of a metal, e.g., a metal foil or metal deposited or painted on a suitable backing. Examples of suitable metals include aluminum, platinum, stainless steel, gold and titanium. Alternatively, electrodes 22 and 24 may be formed of a hydrophobic polymer matrix containing a conductive filler such as a metal powder/flakes, powdered graphite, carbon fibers or other known electrically conductive filler material.

Electrodes 22 and 24 can be applied to the cell and the entire cell can be manufactured by, for example, a suitable printing technology such as, but not limited to, silk print, offset print, jet printing, lamination, materials evaporation or powder dispersion. Accordingly, electrochemical cell 14 as described hereinabove is among the simplest of power sources.

Preferably, electrodes 22 and 24 and the entire cell 14 are printed using any suitable printing technology onto patch 10, resulting in an integrated patch 10.

It is appreciated that each of electrodes 22 and 24 may be of any size and shape, and located with respect to one another, in any arrangement, as may be required to cover the skin portion under treatment. Indeed, in accordance with a preferred embodiment of the present invention, electrochemical cell 14, in conjunction with electrodes 22 and 24, constitute the sole internal elements of patch 10. Accordingly, patch 10 is among the smallest and thinnest active patches and delivers the maximum power per unit of surface area.

Patch 10 of the present invention is preferably supplied within a protective removable or reusable package, or liner, or cover 19, so as to provide physical protection and prolong shelf life prior to use.

Patch 10 is designed and configured to be used with at least one, and preferably many, external substances. Such substances, described in detail hereinafter, are designed to be contained in a conductive fluid, also described in detail hereinafter.

The conductive fluid is designed to be retained in at least one, preferably many, retainers. The combination of patch 10 and the retainer form a kit that may be retained by a patient for use for a variety of applications.

Reference is now made to FIGS. 2*a-g*, which shows a range of retainers for retaining a conductive fluid. The formation of such conductive fluid will generally be "pharmaceutically acceptable" or "physiologically acceptable" formulations for cosmetic or therapeutic use. As used herein, the terms "pharmaceutically acceptable" and "physiologically acceptably" refer to substances that can be administered to a subject, preferably without excessive adverse side effects (e.g., for a topically applied formulation, skin rash, irritation, etc.). Particular formulations include aqueous gels, cream, pastes, lotions, suspensions, emulsions and solutions or other liquid formulations suitable for topical application known in the art.

In a presently preferred embodiment, the conductive fluid is electrically conductive and adhesive hydrogel, suitable for use as a skin contact adhesive and, particularly, suitable for use as an electrical interface for electrodes of medical devices. The hydrogels are cationic acrylates and may be, for example, preferably made from acrylic esters of quaternary chlorides and/or sulfates or acrylic amides of quaternary chlorides. They can be formed by free radical polymerization in the presence of water, preferably by ultra-violet curing with initiator and multi-functional cross-linking agent. The hydrogel may preferably include a buffer system to help prevent discoloration of the hydrogels and/or hydrolysis of the hydrogels and/or to improve shelf-life.

Other additives may be incorporated into the present hydrogels either before or after curing (e.g., conductivity enhancers, pharmaceuticals, humectant plasticizers, etc.) depending on intended end-use. An additive that is preferably added to the hydrogel is a conductive adhesive matter (additive) that serves to allow the conductive fluid to both attach patch 10 to the skin of the subject and to serve as the conductive interface between the electrode and the skin. The adhesive additive is preferably a polymeric adhesive and may be pressure or temperature activatable or it may be activated by the exposure to the ambient atmosphere.

The preferred hydrogel is sufficiently cohesive, yet remains readily separable. Further details pertaining to hydrogels suitable for use in the context of the present invention are described in, for example, U.S. Pat. No. 5,800,685, which is incorporated herein by reference.

In any case, an aqueous conductive fluid in accordance with the teachings of the present invention will typically include water, alcoholic/aqueous solutions, at least one salt or any other charged agent and preferably a buffering medium.

It is appreciated that non-aqueous conductive fluids may also be employed.

The conductive fluids used in conjunction with patch 10 are preferably administered by deposition on one or both electrodes. It is appreciated that the conductive fluid may alternatively or in addition be administered by topical application to the skin. The term "topical" is used herein to refer to administration of a substance on the surface of the skin or mucosal tissue, which can be applied via direct application (e.g., spreading), via an impregnated porous material or object or by spraying or misting. It will be appreciated that topical application of the fluid to the skin of the subject is typically less precise and, if not done carefully, may inadvertently cause an electrical connection between the electrodes directly through the conductive fluid such that the electric current and the mobilized ions would not pass through the skin.

Accordingly, the retainers will vary in shape, size and method of dispensing according to the quantity, application and location relevant to the treatment. Shown in FIGS. 2*b-g* are retainers in the form of a vessel 31 tube 32, jar 33, a container 34, a dispenser 35 and an ampoule 36. It will be appreciated that the present invention contemplates all such retainers as well as others in any shape, size or configuration that serve to retain the conductive fluid and dispense it for use as needed on either the electrodes or upon the skin of a subject.

Figure 2A:
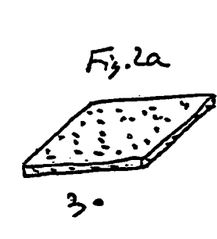
FIGS. 2a-g are illustrations of retainers according to different embodiments of the present invention.
Figure 2B:
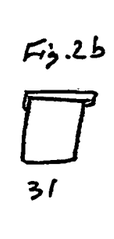
Figure 2C:
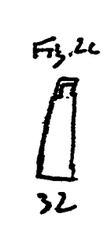
Figure 2D:
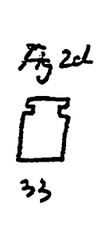
Figure 2E:
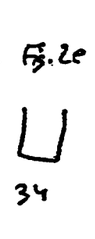

Shown in FIG. 2a is retainer 30 which is a separator. The use of the term "separator" is intended to describe a retainer made of a porous non-conductive material, such as a sponge, paper, etc., that serves to retain the conductive fluid therein. Separators offer advantages over other retainers in that they allow precise positioning of the conductive fluid, they are not messy, and they permit a precise dosage to be administered.

Fluid is retained in a separator in such a manner that objects that are in contact with the separator are also in contact with the fluid contained therein. Accordingly, electrical contact may be made with the conductive fluid held within a separator by establishing physical contact between the electrode and the separator.

Separators are preferably designed and configured to fit between one or both of electrodes 22 and 24 and the skin of the subject, thus providing a simple, clean and convenient electrode/skin interface through which electricity may flow via the conductive fluid to the area of treatment. As stated earlier, separators are constructed so that their non-conductive structure does not impede the electrical contact between electrodes 22 or 24 and the conductive fluid therein. It is understood that a separator will not be positioned such that it or its contents create an electrical contact between electrodes 22 and 24. Such positioning will form an electric circuit that does not include the skin of the subject and will frustrate the purpose of the electrical application.

Separators may be fabricated in the form of plugs, cartridges or tablets and the like which are designed to be compatible with different shapes, sizes and configurations of electrodes 22 and/or 24.

According to a preferred embodiment, retainer 30, in its embodiment as a separator, is preferably a thin waferlike container, which may be of a desired shape to be compatible with both the area of treatment and the electrode in use. Such separators may preferably be protected by a thin film layer, which will be peeled off immediately prior to use.

Separators may be packaged for storage or use as may be compatible with the preferred embodiment of the kit of the present invention. Separators will preferably be individually packaged in order to preserve shelf life and to avoid evaporation of the conducting fluid and/or to substance contained therein.

Figure 2F:
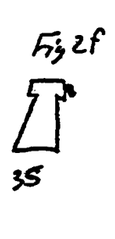
Figure 2G:
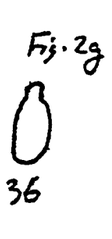
Figure 4A:
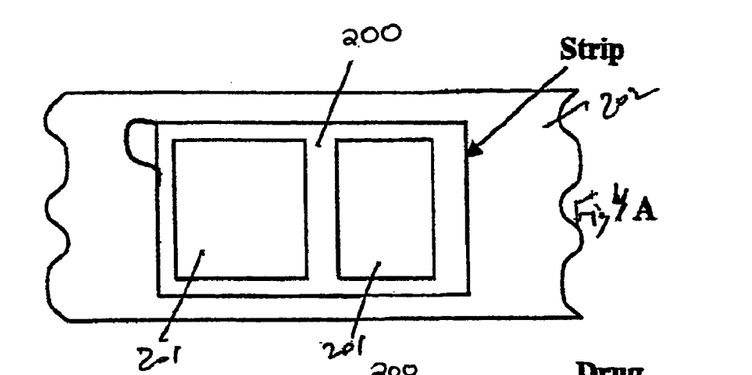
FIGS. 4a-d illustrate a second foolproof embodiment according to the present invention.
Figure 4B:
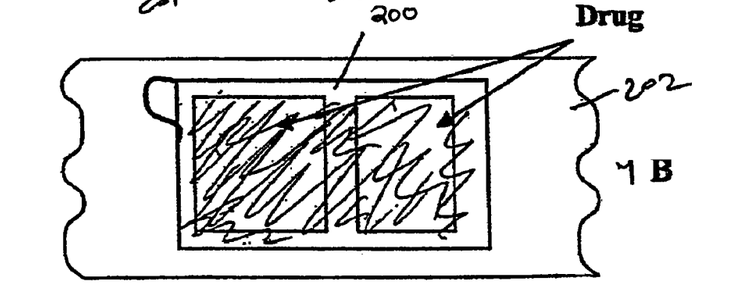
Figure 4C:
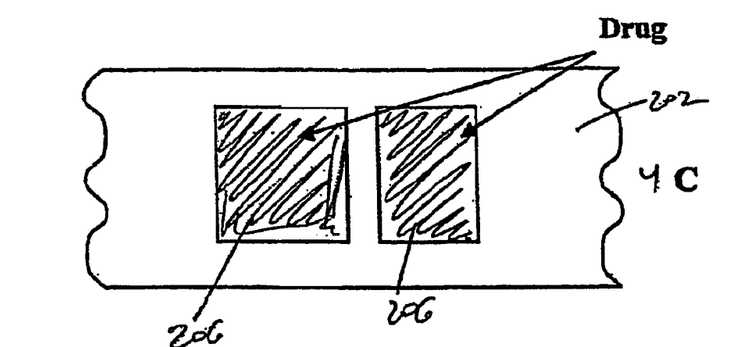
Figure 4D:
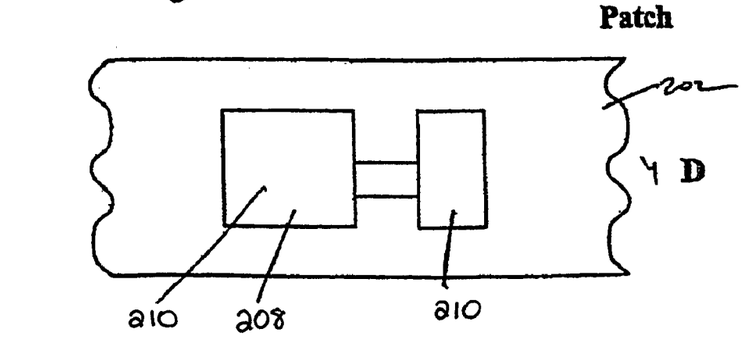

The use of the above described retainers, particularly separator 30, are intended to render patch 10 extremely user friendly and almost foolproof in its employment. The wide variation in the designs and configurations of retainers shown are for the purpose of the precise application of the conductive fluid either on the appropriate electrode or topically upon the skin of the subject. For example, a retainer in the form of tube 32 will permit the simple deposition of a dab of conductive fluid precisely on the electrode. A retainer in the form of ampoule 36 will assure correct dosing of the medicament. Dispenser 35 will permit careful and accurate application of conductive fluid to the exact skin portion of the subject. The preferred embodiment of the invention will have separator 30 as the vehicle for the conductive fluid, which can be positioned with precision on either the electrode or on the skin of the subject.

It is appreciated that the precise positioning of the conductive fluid, either upon the relevant electrode or upon the skin of the subject, is critical to the effective conduction of electric current through the skin of the subject. Accordingly, the kit comprising patch 10 and one or more of retainers 30 through 36 will preferably also contain any other implements, instruction, markings, aids or devices that will serve to assist a user to properly apply and position the conductive fluid as required.

Several foolproof embodiments with respect to patch 10 of the present invention are shown in FIGS. 3a-5c. In the embodiment of FIGS. 3a-d, a strip 100 is placed over the skin 102 and a conductive lotion, gel, cream or the like 104 is applied over the skin 102, such that upon removal of strip 100, two non-contacting zones 106 receptive of a patch 108 constructed and operative in accordance with the teachings of the present invention are formed and patch 108 is applied onto the skin 102, such that the electrodes 110 thereof each being in contact with one of zones 106 so as to avoid a short circuit.

In the embodiment of FIGS. 4a-d, a patterning device 200 having two openings 201 is placed over the skin 202 and a conductive lotion, gel, cream or the like 204 is applied over the skin 202, such that upon removal of patterning device 200, two non-contacting zones 206 receptive of a patch 208 constructed and operative in accordance with the teachings of the present invention are formed and patch 208 is applied onto the skin 202, such that the electrodes 210 thereof each being in contact with one of zones 206, so as to avoid a short circuit.

In the embodiment of FIGS. 5a-c, a foldable patch 308 is placed, in its folded configuration, over the skin 302 and a conductive lotion, gel, cream or the like 304 is applied over the skin 302 on both sides thereof, such that upon flattening patch 308, two non-contacting zones 306 receptive of patch 308 are formed and patch 308 is contacting the skin 302, such that the electrodes 310 thereof each being in contact with one of zones 306, so as to avoid a short circuit.

Figure 6:
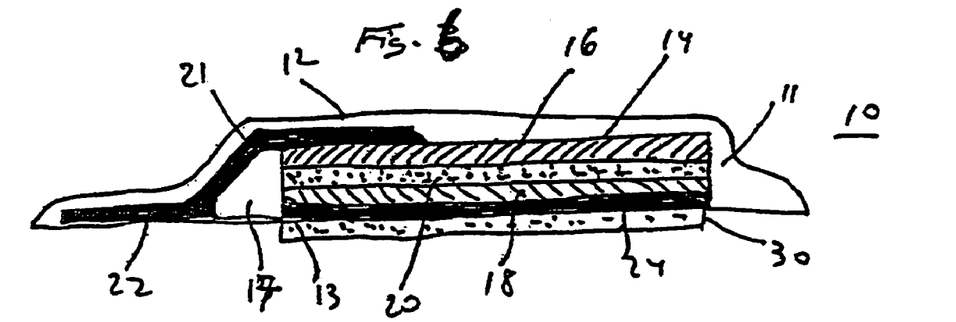
FIG. 6 is a sectional view of a different configuration of a dermal patch according to the present invention.

Reference is now made to FIG. 6 which shows an embodiment of patch 10 of the present invention in which electrode 22 is not integral to electrochemical cell 14 but is connected by a conductive connector, hereinafter referred to as connector 21. Components of patch 10 according to this embodiment of the invention and which are similar to those described above, are not further described and are identified by the same reference numerals as above. Connector 21 may be printed or may be of any conductive material known in the art. According to the illustrated embodiment, the retainer, which is a separator, is deposited on electrode 24 of electrochemical cell 14. Thus, in this configuration, electrode 24 may be referred to as the medical electrode and electrode 22 as the conductive adhesive electrode. According to this embodiment, simultaneous contact with the skin of a subject by electrode 22 and separator 30 will form an electrical circuit which includes the skin of the subject as part of the conductive path. In this configuration, electrochemical cell 14 will produce an electric current which will be delivered through the conductive fluid held by retainer 30 which is in contact with the skin. The electric current will pass through the skin thus mobilizing appropriately charged ions or molecules within the conductive fluid contained therein to pass through the skin.

In an alternative embodiment, the conductive fluid, such as, but not limited to an electrically conductive and adhesive hydrogel is applied directly onto electrodes 22 and 24 during manufacture of patch 10. The applied hydrogel can optionally contain any suitable additive, such as, but not limited to additives previously listed herein. Preferably, water is present in an amount of from about 0 percent to about 100 percent. More preferably water is present in an amount of from about 20 percent to about 60 percent. The resulting patch 10 includes the hydrogel without the need for a separator 30 or retainer. Preferably, patch 10, which includes electrodes 22 and 24 with applied hydrogel is packaged in order to prevent evaporation and drying out of the hydrogel and water. An advantage of a patch produced with hydrogel previously applied on electrodes 22 and 24, is a one-step method of use. Patch 10 is adhered to the skin, closing the electrical circuit and causing current to flow and delivery of a substance, such as, but not limited to water or a pharmaceutical substance contained in the hydrogel. The step of applying hydrogel to the skin or electrode or attaching a retainer is eliminated.

Patch 10, which contains a conductive fluid, preferably aqueous hydrogel, previously applied on electrodes 22 and 24, as described above, can be used on its own without any additional pharmaceutically active substance, to deliver water into the skin. Preferably, the delivery of water into the skin in this way readily facilitates moisturizing of the skin and alleviating of skin conditions, such as, but not limited to skin dryness, skin burns and wrinkles.

One purpose of patch 10 is to transdermally or intradermally deliver a pharmaceutical substance, a cosmetic substance or a cosmeceutical substance. As used herein, the terms "transdermal" and "intradermal" and grammatical variations thereof, respectively refer to the delivery of a composition through/across the skin or into the skin. As used herein, the term "pharmaceutical" refers to therapeutic and anesthetic substances. Therapeutic, as used herein, is understood to include any substance serving to cure, heal, treat medically or preserve health. Anesthetic, as used herein, is understood to include any substance serving to cause a loss of tactile sensation, particularly pain. Such substances, in order to be delivered electrically, will preferably be in the form of charged molecules which will respond to an electric current. It is appreciated that any pharmaceutical substance, cosmetic substance or cosmeceutical substance may be delivered by the invention described herein, as long as the substance is charged or can be charged.

In cases where the substance is not naturally charged it is preferably combined with a charging agent, or subjected to environmental conditions, such as a specific pH environment, which induces charge formation. Methods of charging molecules are well known in the art and as such no further description is given herein. In any case, it is to be understood that the substance to be delivered may be charged prior to or concomitant with its delivery.

Therefore, where used herein the term "substance" refers to active substances which are preferably in the form of charged ions or charged molecules and which are able to be electrically delivered transdermally or intradermally. In general, this includes therapeutic substances in all of the major therapeutic areas including, but not limited to, antiinfectives such as antibiotics and antiviral agents, analgesics including fentanyl, sufentanil, buprenorphine and analgesic combinations, anesthetics, anorexics, antiarthritics, antiasthmatic agents such as terbutaline, anticonvulsants, antidepressants, antidiabetic agents, antidiarrheals, antihistamines, antiinflammatory agents, antimigraine preparations, antimotion sickness, preparations such as scopolamine and ondansetron, antinauseants, antineoplastics, antiparkinsonism drugs, cardiostimulants such as dobutamine, antipruritics, antipsychotics, antipyretics, antispasmodics, including gastrointestinal and urinary, anticholinergics, sympathomimetics, xanthine derivatives, cardiovascular preparations including calcium channel blockers such as nifedipine, beta-blockers, beta-agonists such as salbutamol and ritodrine, antiarrythmics, antihypertensives such as atenolol, ACE inhibitors, diuretics, vasodilators, including general, coronary, peripheral and cerebral, central nervous system stimulants, cough and cold preparations, decongestants, diagnostics, hormones such as parathyroid hormone, growth hormone and insulin, hypnotics, immunosuppressives, muscle relaxants, parasympatholytics, parasympathomimetics, anti-oxidants, nicotine, prostaglandins, psychostimulants, sedatives and tranquilizers. The invention is also useful for the delivery of cosmetic and cosmeceutical substances. Such substances, include, for example, skin acting anti-oxidants, such as caretenoids, ascorbic acid (vitamin C) and vitamin E, as well as other vitamin preparations and other anti-oxidants, anti wrinkling agents such as retinoids, including retinol (vitamin A alcohol), alpha-hydroxic acids, beta-hydroxy acid, better known as salicylic acid, combination-hydroxy acids and poly-hydroxy acids, and hydrolyzed and soluble collagen and others, moisturizers such as hyaluronic acid and others, anticellulite agents such as aminophyllines and others, skin bleaching agents such as retinoic acid, hydroquinone and peroxides and others, botanical preparations such as extracts of aloe-vera, wild yam, hamamelitanin, ginseng, green tea and others.

It is understood that the invention may be used for delivery of a wide range of dosages of the above listed and other substances over a desired duration of time.

The delivery of the substance transdermally or intradermally preferably occurs by a process of iontophoresis and/or electrophoresis. Iontophoresis refers to the-movement of ions caused by the application of an electrical potential. Electrophoresis refers to the movement of charged colloidal particles or macromolecules caused by the application of an electrical field. The electric current caused by the electric potential between electrodes 22 and 24 serves to release the charged substance from the conductive fluid and to deliver the molecules/ions of the charged substance from the conductive fluid and to deliver the molecules into the adjacent skin tissue. The charged substance within the conductive fluid, which is deposited between one or both of electrodes 22 and 24 and the skin of the subject, would be attracted to or repelled by electrode 22 and electrode 24 as appropriate to their charge. For example, if the substance is positively charged, electrode 22 would repel the substance, thus mobilizing it into or through the skin. In this configuration, when current flows from positive electrode 22 in a direction toward the skin, the charged substance is driven across the conductive fluid/skin interface into the skin.

It must be noted that reverse iontophoresis may also be used in a process of transdermal or intradermal recovery of substances from the body. Such a technique employs the same electrical principles applied in reverse. Techniques of transdermal, or intradermal recovery of substances are well known in the art.

The movement of substances transdermally or intradermally may also be aided by a process of electroporation. Electroporation is typically carried out by high voltage pulses applied to a pair of electrodes which are applied to a tissue surface. The electric pulses cause the passing ions to perforate the tissue layer, providing new pathways for the passage of substances, both charged and not charged. It must be noted that electroporation does not deliver a charged substance, but rather reduces the resistance to passage of substances into the adjacent tissue. Because it does not provide a needed driving force, it is desirable that electroporation be combined with delivery techniques such as iontophoresis or electrophoresis in order to achieve good penetration.

Another preferred purpose of patch 10 is to promote wound healing, scar reduction, scar prevention, tissue repair and/or tissue regeneration by direct application of currents through the skin. Electric current has long been known and utilized therapeutically to force excitable cells (nerve, muscles and receptors of nerve ends) of the human body, by electrical stimuli externally supplied in the form of electrical pulses, to generate an electrical response, the so-called action potentials. These action potentials are cell-intrinsic electrical pulses with a defined amplitude and duration for the relevant cell type. For one nerve, for instance, a pulse width of about 1 ms and an amplitude of about 80 mV to 100 mV is typical. The cell reverts to its cell membrane voltage, which at rest, depending on cell type, has a value between 60 mV and 120 mV. This voltage is caused by different ion concentrations in the extracellular and intracellular spaces separated by the cell membrane. More positive ions are found outside the cell. According to definition, the potential outside the cell is set to 0 V, so that a negative potential is given in the cell.

In healthy humans, the action potentials are generated by the body itself and utilized for information transfer and to trigger cellular processes.

In electrotherapy, therapeutic effects are induced by specific generation of action potentials (defined number and at specific loci).

Apparatuses for electrotherapy use a plurality of various electrical currents, or pulse forms. Aiming to choose the electrotherapy best suited for a specific indication, the therapist should be able to revert to criteria of maximally clear definition. These criteria derive from the replies, to questions about the effectiveness and tolerance of the various current form.

The spectrum of effects includes, e.g., the areas of pain alleviation, stimulation of striated and nonstriated muscles, of influencing perfusion, the detumescent mechanisms, of the areas of checking inflammatory processes and of promoting regeneration (wounds, accelerated healing of bones, etc.,) The aim in the application should always be achieving the desired effect in the affected area by proper selection of the current form, either distal or, proximal to the electrode or in the depth of the body.

Basically, electrotherapeutic apparatuses are based on two stimulus current methods, the polarity-dependent "polar stimulation principle" and the polarity-independent "apolar stimulation principle".

Low-frequency alternating currents (LF current) ranging from 0 to 200 Hz are used in the "polar stimulation principle". Hyperpolarization (rise in membrane voltage) occurs beneath the positive electrode, the anode, making the spacing between the potential in the cell and the stimulus threshold greater. In contrast, the membrane voltage drops beneath the negative electrode, the cathode. As the stimulus threshold is reached, the cell triggers automatically an action potential.

Stimulant current apparatuses employ different pulse shapes in the low-frequency spectrum of about >0 to 200 Hz (LF current). Applicable are, e.g., the so-called delta currents, rectangular currents, diadynamic currents, high-voltage currents, ultrastimulant currents, faraday currents—to name but a few. Some alternating currents have a direct current component, which additionally backs the polar effects.

There are two frequency-dependent methods of using action potential's therapeutically:

Functional Imitational Principle:

The number of action potentials generated by the excitable cell (e.g., nerve or muscle) for the performance of its tasks is ascertained. In therapy, the same number of pulses are then generated in the relevant cell by stimulation, thereby backing the cell in performing its tasks.

For instance, a stimulation frequency of up to 6 Hz is applied to generate up to 6 individual contractions per second.

Fatigue Principle:

In contrast, when forcing the cell (nerve or muscle) to generate action potentials, by stimulation at higher frequency and appreciably more often than the cell would be required to do so to perform its tasks, it fatigues after a short time. The opposite effect occurs. The cell fatigue can be explained by energy-consuming processes in the formation of action potentials.

For instance, a sclerosed muscle can be relaxed according to this fatigue principle by stimulating it with a "higher" frequency of, e.g., 100 Hz or 200 Hz.

To generate any action potentials at all, of course, the intensity must be chosen sufficiently high to exceed the stimulus threshold. The level of intensity to be set depends on the following factors: the position (depth) of the cell to be stimulated in the tissue (distance from the electrode), the size of the electrodes and the tissue resistances in the region penetrated by the electric potential, which, in turn, is influenced by the parameters of the current form.

In practice, current form and electrode size are prescribed. To stimulate now a group of cells at a certain distance from the electrode (for example, deep in the tissue), the current and/or voltage intensity continues to be increased until action potentials occur.

As the intensity increases, cells located deeper, and deeper, or cells ever more distal from the electrodes, are being stimulated successively. With the apolar stimulation principle, only so-called medium-frequency alternating currents (MF currents) without any direct current component are employed. Meant by MF currents are sinusoidal alternating currents with a frequency of >5 Hz to 100,000 Hz. A single cycle (alternating pulse) with sufficient intensity has a polar effect which is able to trigger an action potential in a nerve or muscle cell.

Often, a "summation effect" occurs. At increasing frequency, ever higher intensities are needed too, in order to be able to trigger action potentials in the cells. Wyss has proved beyond doubt that the generation of action potentials with MF pulses proceeds entirely independently of polar effects. This means that wherever the intensity and number of oscillations is sufficiently large, action potentials will be generated irrespective of the momentary polarity of the MF current (Wyss, Oscar A. M; Prinzipien der elektrischen Reizung, [Principle of Electrical Stimulation], Neujahrs-Blatt, published by the Natural Research Society in Zurich for the year 1976, Kommissionsverlag Leeman AG, Zurich, 1976, 28-34).

MF pulses are applied at a low-frequency repetition rate of >0 to about 200 Hz and MF carrier frequencies of >5 Hz to 100,000 Hz. In practice, this is mostly a sinusoidal, amplitude-modulated MF current (AM-MF current). The following principles are in agreement with those described in conjunction with the "polar stimulation principle".

Functional-Imitation Principle:

In synchronism with the MF pulses (amplitude modulation), action potentials occur in excitable cells. The cell is thereby induced to exercise its natural functions, which emanate from this frequency.

Fatigue Principle:

To fatigue excitable cells, MF pulses with higher amplitudes are used.

As the current intensity rises, cells are stimulated successively that are located deeper and deeper (more distal from the electrodes).

Along with an increasing the frequency, more intensity is needed to generate action potentials.

On the basis of the medium-frequency alternating current, the following additional options of therapy are given:

When stimulating with (constant-amplitude) MF current of sufficient intensity, an action potential is generated first.

With MF current that flows for a longer time, the decaying flank of the action potential remains at the depolarization level (permanent depolarization), which amounts to about one-half of equilibrium potential. Upon shutting the NM current off, the membrane voltage drops then, delayed, to the level of equilibrium potential.

The following sub-items describe the therapeutic utilization of the permanent depolarization.

Pain Alleviation and Influencing Perfusion:

High intensities which, depending on the properties of the region being treated, range at the tolerance limit cause a blocking of nerve transmission paths, due to the permanent depolarization. This genuine nerve block (proof established by BOWMAN, Bruce R., 1981, dissertation E. K. University of LJubljana, Rancho Los Amigos Hospital, Downey, Calif. U.S.A.) is utilized, e.g., for pain blocking in phantom-limb pains or for stellatum block in blood flow disorders.

Muscular Contraction:

Muscle training in voluntary innervation insufficiency and muscle distention.

With the nerve muscle apparatus intact, the striated muscle (skeletal muscle) is stimulated directly by permanent depolarization. This results in muscle contraction, which is used, e.g., in voluntary innervation insufficiency of the muscles or to stretch the antagonists of spastic muscles. During treatment, the, intensity should be interrupted by pauses in short intervals. The intensity also may be increased and decreased between 100% and about 50% of the adjusted value.

Generating Strong Muscle Contraction Forces:

Very strong muscle contractions may be induced without fatigue phenomena. In tetanic contraction, which can be induced with stimulation current of about 50 Hz and up, a rapid decrease of the muscle contraction force occurs contrarily, due to fatigue of the myokinetic units.

Cell Division:

Wound Healing and Accelerated Bone Healing:

Permanent depolarization induces cell division in healthy cells. Wound healing may be promoted thereby, bone healing accelerated in fractures. Moreover, MF currents induce under the effect of the electrical alternating field reciprocal movement (shaking effect) of charged molecules in the current penetrated tissue, accompanied by rotation movements of the charged molecule shares. Achieved thereby is a greater probability of a "correct" meeting position of enzyme and substrate, which in metabolic processes interact chemically (metabolic facilitation). This shaking effect tends to level differences in concentration, in that diffusion processes which on account of existing concentration gradients proceed in certain directions are accelerated due to the kinetic energy that is additionally imparted (MF iontophoresis, inhibition of inflammation, alleviation of pain).

The shaking effect is especially effective at high intensities.

Distribution of Inflammatory and Pain Mediators:

Inhibition of Inflammation and Alleviation of Pain:

In painful, inflammatory processes a high concentration of inflammatory and pain mediators is regularly found in the diseased tissue. This high concentration is reduced (dispersed) by the shaking effect. Caused by high current intensities, the "shaking intensity" —the same as the frequency— is of great significance for the therapeutic effects (Hans-Jurgens, May, Elektrische Differential-Therapie [Electrical Differential Therapy], Karlsruhe 1990).

Influencing of Metabolism (Diffusion, Mitochondria, Cyclic AMP):

Facilitation and Promotion of Metabolic Processes:

As described above, the biochemical metabolic processes are facilitated.

Also in penetrating cell cultures with MF current it has been found that the number of mitochondria ("energy plants" of the cells) and their size increase significantly.

The concentration of an important messenger substance of the cell, the cyclic AMP, can also be influenced by alternating current, depending on MF current and/or voltage (Dertinger, 1989, Kemforschungszentrum Karlsruhe, Nagy Nemectron GmbH Karlsruhe).

Furthermore, a painless and strong muscle contraction can be induced with MF currents.

The so-called "threshold dissociation" occurs from 8 kHz, that is, the threshold amperage for muscle contraction goes below that of the sensible threshold (Edel, H.: Fibel der Elektrodiagnostik and Elektrotherapie Primer of Electrodiagnostics and Electrotherapy, Muller & Steinicke Munchen 1983, p. 193). Strong muscle contractions can be induced without pain. Viewed therapeutically, threshold dissociation is of particular interest in utilizing the reversible process of muscle contraction, which is caused by the permanent depolarization of the MF current.

Due to the high intensities of the MF current, heat is generated in the current-penetrated tissue. But a prerequisite is that the patient not be discomforted by exceeding the thresholds (sensation, muscle, tolerance, pain).

Analogous to the improvement of the metabolic processes, also an iontophoresis can be accomplished with MF current, i.e., the administration of medications with the aid of current through the skin into the body. Owing to the physical circumstances, iontophoresis with MF current requires a longer treatment time and higher intensities as compared to galvanic current.

As described above and found insofar also in the pertaining trade literature (refer to book "Elektrische Differential-Therapie" [Electrical Differential Therapy] by A. Hansjuorgens and H. U. May, 1990; Nemectron GmbH, Karlsruhe), the prior electrotherapeutic apparatuses employ, depending on diagnosis, low-frequency currents or amplitude-modulated medium-frequency currents at frequencies >0 to 200 Hz or medium-frequency currents at a frequency of >5 Hz to 100,000 Hz, each with constant amplitude (intensity).

Because any one and more of the above uses is anticipated for dermal patch of the present invention, patch 10 preferably includes electrical circuitry for controlling the level or duration of current produced by electrochemical cell 14. Such circuitry may take the form of an on-off switch for "on-demand" drug delivery (e.g., patient controlled delivery of an analgesic for pain relief), a timer, a fixed or variable electrical resistor, a controller which automatically turns the device on and off at some desired periodicity to match the natural or circadian patterns of the body, or other more sophisticated electronic control devices known in the art. For example, it may be desirable to deliver a predetermined constant level of electric current since a constant current level ensures a constant rate of substance delivery. The level of current can be controlled by a variety of known means, for example, a resistor or a simple circuit that employs a resistor and a field effect transistor. The circuitry may also include an integrated circuit which could be designed to control the dosage of active agent delivered, or even to respond to sensor signals in order to regulate the dosage to maintain a predetermined dosage regimen. A relatively simple circuit can control the current as a function of time, and if desired, generate complex current waveforms such as pulses or sinusoidal waves as is further described above. In addition, the circuitry may employ a bio-feedback system which monitors a biosignal, provides an assessment of the therapy, and adjusts the active agent delivery accordingly. A typical example is the monitoring of the blood sugar level for controlled administration of insulin to a diabetic patient. A simple yet important use of a controlling circuit is the avoidance of heat buildup and resultant tissue damage. It is understood that the delivery of ions causes heat due to the movement of the ions and that the greater the delivery, the greater will be the heat buildup at the site of the delivery. As such, the current used for treatment could be patient-controlled such that a balance may be found between maximizing the delivery of substance and minimizing the discomfort of temperature increase.

A kit according to the present invention will therefore include a dermal patch-for the transdermal and/or intradermal delivery of at least one substance, and at least one retainer for retaining the substance(s) away from the patch prior to use. This construction allows the versatile use of substances/dosages with a single dermal patch.

A method of transdermal or intradermal delivery of at least one substance according to the present invention is hence effected by (a) topically applying a conductive fluid containing the substance onto a skin portion of the subject and/or depositing the conductive fluid containing the substance on at least one electrode of a dermal patch which, includes an, electrochemical cell having at least two electrodes positioned on one side of the dermal patch; (b) positioning the dermal patch such that the electrodes are in electrical contact with the skin portion of the subject; and (c) delivering an electric current through the conductive fluid and the skin portion so as to transdermally or intradermally deliver the substance.

A method of introducing current and/or voltage to a skin portion of a subject according to the present invention is hence effected by (a) topically applying a conductive fluid onto a skin portion of the subject and/or depositing the conductive fluid on at least one electrode of a dermal patch which comprises an electrochemical cell having at least two electrodes positioned on one side of the dermal patch; (b) positioning the dermal patch such that the electrodes are in electrical contact with the skin portion of a subject; and (c) delivering an electric current through the conductive fluid so as to introduce current and/or voltage to the skin portion of the subject.

It is understood that the conductive fluid may be deposited onto one or both electrodes either being retained within the retainer or by being: dispensed from any of the other retainers described. It is further understood that the above applications of the present invention may also be effected by topically applying the conductive fluid to the skin at the location that the electrode will be placed.

The present invention offers numerous advantages over existing patches which inherently include substances to be transdermally or intradermally delivered as a single dermal patch can be used to deliver any number of different substances/doses as long as it is powered, it need not be discarded as it is never depleted.

Additional objects, advantages, and novel features of the present invention will become apparent to one ordinarily skilled in the art upon examination of the following examples, which are not intended to be limiting. Additionally, each of the various embodiments and aspects of they present invention as delineated hereinabove and as claimed in the claims section below finds experimental support in the following examples.

EXAMPLES

Reference is now made to the following examples, which together with the above descriptions, illustrate the invention in a non limiting fashion.

Example 1

Treatment of Mild Rosacea

Mild rosacea, characterized by redness of parts of the face and telangectasia, is a common disorder, afflicting many individuals, mainly from the aging population. Unfortunately the treatments for mild rosacea are limited.

Three patients with mild rosacea were enrolled in a pilot study, meeting the following inclusion criteria:

Patient has mild to moderate redness in both sides of the face; and

Patient is between 20 and 65 years of age.

The study objectives were to detect the therapeutic effects on the redness phenomenon, during and following treatment and to detect side effects.

Each study subject received treatment of both sides of the face.

On one side of the face an "Active Patch", linked by thin cords to a power supply so that the large part of the patch (Main Patch) was linked to the Positive pole of the power supply and the small part of the patch (Counter-Patch) was linked to the negative pole of the power supply.

A "Passive Patch", with same shape, without being connected to an electrical source, was used on the other side of the face of each tested subject.

Each patch was coated by a Test Preparation (aqueous gel, containing witch hazel extract). 0.4 ml of the Test Preparation was evenly applied onto the Main Patch and 0.1 ml to the Counter Patch, using a spatula. The patches were then applied onto the skin of the study subjects for a period of 7-20 minutes (the Treatment Period).

Observations were taken immediately after removal of the patches and 10, 25 and 40 minutes thereafter, including subjective assessment by the patient and blinded assessment by a trained observer. Photographs were taken prior to treatment and at all observation points.

In all three patients, there was a pronounced reduction in the degree of redness and the extent of telangectasia at the Active Patch sites. This improvement was first observed immediately after patch removal and further documented for the rest of the observation period. The Passive Patch sites exhibited very slight improvements, which were not considered by the patients or the observer as significant.

Example 2

Treatment of Hyperhidrosis

It is estimated that about 1% of the population suffer from hyperhidrosis—excessive sweating. The great majority suffer from localized hyperhidrosis, which mainly affects the axillae the feet and the hands. On the feet excessive sweating can trigger a host of dermatological disorders. Sweaty hands can cause social and esteem problems and can be a safety hazard.

Treatment of hyperhidrosis include the use of antiperspirants, aluminum chloride, systemic treatment with minor sedatives, anticholinergics, botox injections and iontophoresis, as described in *International Journal of pharmaceutical Compounding*, Vol. 5, No. 1, January/February 2001, p. 28-29.

Use of the kit or dermal patch of the present invention is effective in the treatment of hyperhidrosis. Preferably, the patch or kit is used with tap water resulting in iontophoretic treatment of palmar or plantar hyperhidrosis. Optionally, any type of water is envisioned for use with the dermal patch and kit of the present invention, such as, but not limited to tap water, distilled water, cooled boiled water or mineral water may be used. In some circumstances it may be preferable to have a mixture of water and an additional active ingredient or additive, such as but not limited to any suitable non-toxic anti-sweating agent.

The water is preferably contained in the hydrogel to form an aqueous hydrogel. The aqueous hydrogel can optionally be applied directly to the desired area of the body. Alternatively, the aqueous hydrogel is preapplied, such as, but not limited to, during manufacture of the patch, onto the electrodes of the patch and therefore the patch is ready for use. Further, the aqueous hydrogel can be contained in a separator, which is integrally formed with the patch. Still further, the aqueous hydrogel can be contained in a separate retainer, such as is used in the dermal kit. The retainer is then connected to the patch before use.

A typical method of treatment includes the following steps of adhering the patch of the present invention to the desired area of the body, such as, but not limited to the hand, foot and underarm. One area or more than one area of the body can be treated at the same time using a plurality of patches. If the dermal kit of the present invention, which includes a separate retainer is being used, the retainer which preferably contains aqueous conductive hydrogel and water is first attached to the patch before adhering to the skin. In the case where a patch of the present invention is being used, which does not include hydrogel, the aqueous hydrogel can be applied directly to the place of treatment on the body of the subject. In the case that the hydrogel is contained in the patch, the patch is ready to use.

Adhering the patch to the skin closes the electrical circuit. Current will then flow, resulting in iontophoresis and electrical stimulation of the skin. The duration of treatment is determined according to severity of condition and other skin factors. A typical treatment session lasts between about 10 to about 20 minutes. Treatment is terminated by removal of the patch. Alternatively, treatment is terminated by depletion of the battery, at least one of the electrodes or depletion of the aqueous hydrogel.

Typically, the treatment is repeated in selected time intervals over about a month. At the beginning, the treatment is usually repeated more frequently, such as a few times a week and then for maintenance of the resulting anti-sweating effect, the treatment is repeated less frequently.

While the exact mechanism for the effects of tap water iontophoresis on hyperhidrosis remains uncertain, one hypothesis is that a parakeratotic plug is formed, blocking the duct without damaging the sweat gland.

The patch of the present invention is optionally configured to any suitable size and shape. Optionally, the patch can be connected to or integrally formed with an article of clothing that is in contact with the area of symptomatic hyperhidrosis, such as, but not limited to a shoe, in the form of a shoe sole insert, in a glove, sock, tights, underarm sleeve portion of an article of clothing or a combination thereof. Optionally, the patch is removable from the clothing. The patch can be optionally for one time use or reusable. Preferably, the patch is disposable.

The patch of the present invention offers several advantages over the available iontophoretic devices, which have been used in the treatment of hyperhidrosis. Firstly, the patch is flexible and therefore fits much better into the contours of the feet, arms and armpits, ensuring more uniform treatment. Secondly, the patch and kit of the present invention are light and compact and user friendly, readily facilitating easy home use, without the need of a professional. In addition, wherein the aqueous hydrogel is contained in the patch, the treatment is a one-step treatment, without the need for messy application of water or aqueous hydrogel. Moreover, an integrated clothing patch readily facilitates concealed on the spot treatment, which also has psychological benefits for the patient who is often embarrassed by the symptoms of this condition.

Example 3

Iontophoretic Treatment 2 of Hyperhidrosis

Treatment of hyperhidrosis include the use of antiperspirants, aluminum chloride, systemic treatment with minor sedatives, anticholinergics, botox injections and iontophoresis, as described in *International Journal of Pharmaceutical Compounding*, Vol. 5, No. 1, January/February 2001, p. 28-29.

Use of the kit or dermal patch of the present invention is effective in the treatment of hyperhidrosis. Optionally, the patch or kit can be used for the iontophoretic delivery of anti hyperhidrosis active substances, which are usually used topically or systemically in the treatment of hyperhidrosis, such as, but not limited to aluminum chloride, anticholinergics and a combination thereof.

The substance to be administered, such as aluminum chloride is optionally contained in the hydrogel, which is either preapplied to the electrodes or is administered onto the skin. Further, the substance to be administered can be contained in a separator, which is integrally formed with the patch. Still further, the substance to be administered can be contained in a separate retainer, such as is used in the dermal kit. The retainer is then connected to the patch before use.

A typical method of treatment includes the following steps of adhering the patch of the present invention to the desired area of the body, such as, but not limited to the hand, foot, underarm or a combination thereof. One area or more than one area of the body can be treated at the same time using a plurality of patches. If the dermal kit of the present invention, which includes a separate retainer is being used, the retainer which contains aqueous conductive hydrogel and active substance to be delivered is first attached to the patch before adhering to the skin. In the case where a patch of the present invention is being used, which does not include hydrogel or the active substance to be delivered, the mixture is applied directly to the place of treatment on the body of the subject. In the case wherein the hydrogel and active substance to be delivered is contained in the patch, the patch is ready to use.

Adhering the patch to the skin closes the electrical circuit. Current will then flow, resulting in iontophoretic delivery of the active substance, such as the anti-cholinergic or aluminum chloride and electrical stimulation of the skin. The duration of treatment is determined according to severity of condition and other skin factors. Treatment is terminated by removal of the patch. Alternatively, treatment is terminated by depletion of the battery, at least one of the electrodes or depletion of the active substance to be delivered.

Typically, the treatment is repeated in selected time intervals over about a month. At the beginning, the treatment is usually repeated more frequently, such as a few times a week and then for maintenance of the resulting anti-sweating effect, the treatment is repeated less frequently.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable subcombination.

It will be appreciated by persons skilled in the art that the present invention is not limited to what has been particularly shown and described hereinabove. Rather, the scope of the present invention is defined by the appended claims and includes both combinations and subcombinations of the various features described hereinabove as well as variations and modifications thereof which would occur to persons skilled in the art upon reading the foregoing description. Accordingly, it is intended to embrace all such alternatives, modifications and variations that fall within the spirit and broad scope of the appended claims.

What is claimed is:

1. A dermal patch comprising at least one power source comprising an electrochemical cell for powering the patch, wherein the electrochemical cell comprises a negative pole, a positive pole, and an electrolyte and at least two electrodes spaced apart and in electrical connection with the electrochemical cell, the electrodes for electrically coupling to a skin portion and/or skin appendage of a subject, wherein at least one of the at least two electrodes is integrally formed on or with the electrochemical cell.

2. The dermal patch of claim 1 further comprising at least one retainer for retaining a substance and for preventing contact between at least one of the at least two electrodes and the skin portion.

3. The dermal patch of claim 1 for introducing current and/or voltage to the skin portion of the subject.

4. The dermal patch of claim 3, wherein the patch further comprises circuitry for controlling the current.

5. The dermal patch of claim 1 for at least one of dermal delivery, transdermal delivery and intradermal delivery or a combination thereof of at least one substance to the skin portion of the subject.

6. The dermal patch of claim 5, wherein the at least one substance is selected from the group consisting of a pharmaceutical, a cosmetic, a cosmeceutical and moisture.

7. The dermal patch of claim 5 wherein the at least one substance is at least one of an analgesic, anesthetic, hormone, muscle relaxant, anti-wrinkling agent, moisturizer, anticellulite agent, skin bleaching agent, antibiotic, antiinfective, antiviral agent or salicylic acid.

8. The dermal patch of claim 5, wherein the at least one substance is at least one of antiinfectives, antibiotics, antiviral agents, analgesics, fentanyl, sufentanil, buprenorphine, analgesic combinations, anesthetics, anorexics, antiarthritics, antiasthmatic agents, terbutaline, anticonvulsants, antidepressants, antidiabetic agents, antidiarrheals, antihistamines, antiinflammatory agents, antimigraine preparations, antimotion sickness, scopolamine, ondansetron, antinauseants, antineoplastics, antiparkinsonism drugs, cardiostimulants, dobutamine, antipruritics, antipsychotics, antipyretics, antispasmodics, gastrointestinal and urinary, anticholinergics, sympathomimetics, xanthine derivatives, cardiovascular preparations, calcium channel blockers, nifedipine, beta-blockers, beta-agonists, salbutamol, ritodrine, antiarythmics, antihypertensives, atenolol, ACE inhibitors, diuretics, vasodilators, coronary, peripheral and cerebral, central nervous system stimulants, cough and cold preparations, decongestants, diagnostics, hormones, parathyroid hormone, growth hormone, insulin, hypnotics, immunosuppressives, muscle relaxants, parasympatholytics, parasympathomimetics, anti-oxidants, nicotine, prostaglandins, psychostimulants, sedatives, tranquilizers, skin acting anti-oxidants, caretenoids, ascorbic acid (vitamin C), vitamin E, anti wrinkling agents, retinoids, retinol (vitamin A alcohol), alpha-hydroxic acids, beta-hydroxy acid, salicylic acid, combination-hydroxy acids and poly-hydroxy acids, and hydrolyzed and soluble collagen, moisturizers, hyaluronic acid, anticellulite agents, aminophyllines, skin bleaching agents, retinoic acid, hydroquinone, peroxides, botanical preparations, extracts of aloe-vera, wild yam, hamamelitanin, ginseng, witch hazel, water and green tea.

9. The dermal patch of claim 1, wherein the patch is a thin and flexible patch.

10. The dermal patch of claim 1, wherein the at least two electrodes are integrally formed with the electrochemical cell.

11. The dermal patch of claim 1, wherein the patch further comprises a patch body and wherein the power source and the at least two electrodes are disposed on the patch body in spaced relation to each other to define a gap between the at least two electrodes.

12. The dermal patch of claim 11, wherein the at least two electrodes are applied to the patch body using a printing technique.

13. The dermal patch of claim 11, wherein the dermal patch is an integrated patch comprising the electrochemical cell and the at least two electrodes applied onto the patch using a printing technology.

14. The dermal patch of claim 1, wherein the patch further comprises an attachment mechanism for attaching the patch to the skin portion of the subject.

15. The dermal patch of claim 1, wherein the electrochemical cell comprises a flexible thin layer electrochemical cell.

16. The dermal patch of claim 15, wherein the flexible thin layer electrochemical cell is a flexible thin layer open liquid state electrochemical cell which comprises a first layer of insoluble negative pole, a second layer of insoluble positive pole and a third layer of aqueous electrolyte, the third layer being disposed between the first and second layers and including:
  (a) a deliquescent material for keeping the open cell wet at all times;
  (b) an electroactive soluble material for obtaining required ionic conductivity; and
  (c) a water-soluble polymer for obtaining a required viscosity for adhering the first and the second layers to the third layer.

17. The dermal patch of claim 1, packaged and identified for an application selected from the group consisting of a wound healing application, a scar prevention application, a scar reduction application, a tissue repair application, a tissue regeneration application, muscle stimulation, muscle contraction, accelerated bone healing, treatment of hyperhidrosis, inhibition of inflammation, facilitation and promotion of metabolic processes, pain alleviation, and treatment of rosacea, wrinkles, skin dryness, skin burns and telangiactasia.

18. The dermal patch of claim 1 further comprising a conductive fluid.

19. The dermal patch of claim 18, wherein the conductive fluid comprises at least one substance.

20. The dermal patch of claim 19 wherein the conductive fluid is preapplied to the at least two electrodes and wherein on contacting the patch with skin an electric current is delivered through the conductive fluid and skin of a subject so as to transdermally or intradermally deliver the at least one substance.

21. The dermal patch of claim 18, wherein the conductive fluid is an aqueous hydrogel.

22. The dermal patch of claim 21, wherein the aqueous hydrogel is applied during manufacture of the patch.

23. The dermal patch of claim 1 for recovery of substances from the body.

24. The dermal patch of claim 1, wherein at least one of the at least two electrodes is a terminal of the electrochemical cell.

25. The dermal patch of claim 1, wherein the at least two electrodes are both terminals of the electrochemical cell.

26. The dermal patch of claim 1, wherein the patch is foldable.

27. The dermal patch of claim 1, wherein the power source and the at least two electrodes are the only constituents of the patch.

28. A method of use of a dermal patch of claim 1, the method comprising:
    (a) positioning the dermal patch such that the electrodes are conductively coupled to the skin portion of the subject; and
    (b) delivering an electric current to the skin portion of the subject.

29. The method of claim 28, further comprising promoting delivery of at least one substance to the skin portion.

30. The method of claim 28, wherein there is no separate step of the user applying hydrogel to the skin or electrode.

31. A kit for introduction of an electric current and/or voltage to a skin portion and/or transdermal or intradermal delivery of at least one substance comprising:
    (a) a dermal patch of claim 1; and
    (b) at least one retainer for retaining a conductive fluid.

32. The kit of claim 31, wherein the conductive fluid contains the at least one substance and wherein the retainer is a separator for deposition upon the skin portion such that, upon contact by the separator with at least one of the at least two electrodes, the electric current causes the transdermal or intradermal delivery of the at least one substance.

33. The kit of claim 31, wherein the conductive fluid contains the at least one substance and wherein the retainer is a separator for deposition on at least one of the at least two electrodes such that, upon contact by the separator with the skin portion, the electric current causes the transdermal or intradermal delivery of the at least one substance.

34. The kit of claim 31, wherein the retainer is a separator and the separator is contained in a removable cover.

* * * * *

UNITED STATES PATENT AND TRADEMARK OFFICE
CERTIFICATE OF CORRECTION

PATENT NO.        : 7,643,874 B2                                       Page 1 of 1
APPLICATION NO. : 10/757414
DATED             : January 5, 2010
INVENTOR(S)       : Nitzan et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1694 days.

Signed and Sealed this

Twenty-first Day of December, 2010

David J. Kappos
*Director of the United States Patent and Trademark Office*